(12) United States Patent
Faridoon

(10) Patent No.: US 9,161,882 B2
(45) Date of Patent: Oct. 20, 2015

(54) THERAPEUTIC SHOWER AND METHOD OF USING THE SHOWER FOR WEIGHT REDUCTION

(71) Applicant: Husain S. A. Faridoon, Safat (KW)

(72) Inventor: Husain S. A. Faridoon, Safat (KW)

( * ) Notice: Subject to any disclaimer, the term of this patent is extended or adjusted under 35 U.S.C. 154(b) by 261 days.

(21) Appl. No.: 13/852,708

(22) Filed: Mar. 28, 2013

(65) Prior Publication Data

US 2013/0226109 A1    Aug. 29, 2013

Related U.S. Application Data

(63) Continuation-in-part of application No. 13/305,867, filed on Nov. 29, 2011, now abandoned.

(51) Int. Cl.
*A47K 3/022* (2006.01)
*A61H 33/06* (2006.01)
*A61N 5/06* (2006.01)
*A61H 9/00* (2006.01)
*A61H 35/00* (2006.01)

(52) U.S. Cl.
CPC .............. *A61H 33/06* (2013.01); *A47K 3/022* (2013.01); *A61H 9/0007* (2013.01); *A61H 35/00* (2013.01); *A61N 5/0625* (2013.01); *A61H 33/066* (2013.01); *A61H 2009/0035* (2013.01); *A61H 2033/061* (2013.01); *A61H 2201/0207* (2013.01); *A61H 2201/0228* (2013.01); *A61H 2203/0406* (2013.01); *A61H 2203/0456* (2013.01); *A61N 2005/0659* (2013.01); *A61N 2005/0668* (2013.01)

(58) Field of Classification Search
CPC ...................................................... A47K 3/281
USPC ....................................................... 4/596–614
See application file for complete search history.

(56) References Cited

U.S. PATENT DOCUMENTS

| 944,611 | A | | 12/1909 | Holmes |
|---|---|---|---|---|
| 1,331,018 | A | | 2/1920 | Luthy |
| 1,728,129 | A | * | 9/1929 | Madison ........................... 4/558 |
| 1,944,611 | A | | 1/1934 | Reinartz et al. |
| 2,949,109 | A | * | 8/1960 | Koolnis ........................ 601/156 |
| 3,587,118 | A | * | 6/1971 | Compton ........................... 4/604 |
| 3,858,252 | A | | 1/1975 | Ejchorszt |
| 4,733,421 | A | * | 3/1988 | Kuersteiner ................... 15/88.3 |
| 4,809,369 | A | | 3/1989 | Bowden |
| 4,871,900 | A | * | 10/1989 | Hickman ...................... 392/380 |
| 5,099,587 | A | * | 3/1992 | Jarosch ........................... 34/202 |
| 5,255,399 | A | * | 10/1993 | Park .................................. 4/525 |
| 5,909,969 | A | * | 6/1999 | Davison ........................... 4/569 |
| 6,567,998 | B2 | * | 5/2003 | D'Ugo .............................. 4/569 |
| 6,623,511 | B1 | * | 9/2003 | Daffer et al. .................... 607/82 |

(Continued)

*Primary Examiner* — Lori Baker
(74) *Attorney, Agent, or Firm* — Hauptman Ham, LLP

(57) ABSTRACT

A therapeutic shower assembly for weight reduction contemplates a generally horizontal support for an individual's body in a horizontal position on their back or stomach and a shower enclosure that accommodates the support. The shower enclosure also includes a source of pressurized water or a pump, a water heater for providing heated water and a horizontal serpentine pipe including a plurality of upwardly directed small openings. The assembly also includes two valves for stopping the flow of water to a portion of the pipe and the second valve for totally stopping the flow of water. The upwardly directed heated water falls gently on the individual. A mechanism raises and lowers the serpentine pipe to allow access to the support and to bring the pipe within about a foot or two of the individual. Finally, a timer and alarm warn an individual that the treatment is over.

10 Claims, 4 Drawing Sheets

(56) References Cited

U.S. PATENT DOCUMENTS

| | | |
|---|---|---|
| 6,681,417 B2 | 1/2004 | Brunelle et al. |
| 6,962,005 B1 * | 11/2005 | Khosropour et al. ........... 34/218 |
| 7,013,504 B2 | 3/2006 | Brunelle et al. |
| 7,454,803 B2 | 11/2008 | Guerin et al. |
| 2003/0188378 A1 * | 10/2003 | Brunelle et al. ................. 4/597 |
| 2004/0060107 A1 | 4/2004 | Eisenberg |
| 2004/0107496 A1 | 6/2004 | Brunelle et al. |
| 2006/0064815 A1 * | 3/2006 | Guerin et al. .................... 4/596 |
| 2008/0072376 A1 | 3/2008 | Guerin et al. |
| 2010/0018588 A1 * | 1/2010 | Lee et al. ...................... 137/338 |

* cited by examiner

THERAPEUTIC SHOWER AND METHOD OF USING THE SHOWER FOR WEIGHT REDUCTION

CROSS REFERENCE TO RELATED APPLICATIONS

The present application is a Continuation-In-Part of U.S. patent application Ser. No. 13/305,867, filed on Nov. 29, 2011, and priority is hereby claimed under 35 U.S.C. §120 based on this application and is hereby incorporated by reference in its entirety into the present application.

FIELD OF THE INVENTION

This invention relates to a therapeutic shower assembly and a method for weight reduction using such showers several times a day and more particularly to a therapeutic shower assembly for subjecting a human body to relatively low pressure heated droplets of water over a majority of the body for a preselected period of time several times a day to melt fat cells and increase circulation.

BACKGROUND OF THE INVENTION

Full body showers and therapeutic shower systems are known and have been in use for a number of years. For example, an early shower structure is disclosed in a U.S. Patent of Ejchorszt U.S. Pat. No. 3,858,252. As disclosed an improved shower structure that may be used as a replacement for a conventional shower head or installed initially as an integral part of a bathroom, the shower structure permits the user to selectively direct a uniform spray of heated water over a desired portion of the body and is particularly adapted for the use of a woman and elderly persons who may now take a shower without getting their hair and head wet. Further, the shower structure is adapted for being formed as an integral part of a wall structure to direct a spray of water over the trunk portions of a user.

A full body shower is disclosed in a U.S. Patent of Davison U.S. Pat. No. 5,909,969. The Davison patent discloses a full body shower system having three generally horizontal water dispensing portions and two generally vertical closed portions connecting the horizontal portions. The maximum number of water spray apertures in the system is sixty. The apertures are located in the horizontal water dispensing portions at angles with respect to the horizontal to direct water in a predetermined pattern.

Finally, a U.S. Patent of Brunelle et al. U.S. Pat. No. 7,013,504 discloses a therapeutic shower enclosure wherein a top wall assembly converts a shower enclosure into a therapeutic shower enclosure. The top wall assembly has an air blower in communication with one or more air return orifices in the top wall. An air distribution channel is in communication with an air blower and at least one air injecting orifice is provided in the top wall and communicates with the enclosure. A heater is provided in the air distribution channel for heating convected air therein to a temperature of up to about 75° C. to provide a stream of hot dry air circulating in the enclosure about a person's body standing therein. This causes the person's body to transpire and provide a therapeutic effect of shedding toxins through the skin. In combination with the hot dry treatment there is available chromotherapeutic and luminotherapeutic light treatment and an ion and ozone generator to inject ions and ozone into the hot dry air stream.

Notwithstanding the above, it is presently believed that there is a need and a potential commercial market for a therapeutic shower assembly or device and for an improved method for losing weight associated with the improved shower assembly according to the invention. There should be a need and a potential commercial market for the improved shower assembly because it provides an additional approach to weight reduction without the use of pills and/or exercises that may be overly stressful for some individuals. Further, the therapeutic shower assembly in accordance with the present invention is rugged, easy to use and can be manufactured and sold at a reasonable cost.

BRIEF SUMMARY OF THE INVENTION

In essence, the present invention contemplates a therapeutic shower assembly for weight reduction that comprises or consists of means for providing heated water under relatively low pressure and means for directing a spray of heated water upwardly at relatively low pressure onto a majority of a human body. The means for directing a spray of water onto a majority of a human body includes multiple arrays of generally horizontally disposed openings disposed at multiple levels and adapted to direct a spray of water in a slightly elevated manner as for example, at an angle of about 30 to 45 degrees above horizontal. The shower assembly also includes means for stopping the spray of heated water and means for drying the human body. The drying means may include a blower for directing heated air around the human body and/or a series of infrared lamps to heat the air directed onto the human body to surround the body with heated air.

In a preferred embodiment of the invention, the therapeutic shower assembly provides a source of water and a water heater 21 for raising the temperature of the water to a temperature of about 25° C. to 30° C. (77° F. to 86° F.). A one-half horse power water pump and means for directing a spray at relatively low pressure including a plurality of droplets of water onto the person's body. In the preferred embodiment of the invention, a plurality preferably ten generally horizontal sections of one-half inch diameter pipe are connected together in a serpentine arrangement by nine generally horizontal pipes and wherein the pipes are connected to the water pump and the ten horizontal sections include a total of about 100 slightly upwardly directed apertures and wherein each aperture has a diameter of about 0.12 inches for spraying droplets of heated water onto a majority of the human body. A heater 18 for directing heated air onto the human body to dry the human body include a plurality of vents that direct heated air to various parts of the body.

In the preferred embodiment of the invention, the shower stall has a width of a little over 72 inches (182.88 cms) and a depth of about 36 inches (91.44 cms) and contains a horizontal support with a plurality of openings for supporting an individual in a horizontal position lying on an individual's back or stomach. The apparatus also includes one or more valves for preventing droplets of water from falling on an individual's face and head.

This embodiment also includes a plurality of small openings in the primary portions of the parallel pipes so that the sprays of water are directed upwardly by about 45° above horizontal and fall downwardly onto the individual for a period of 2½ to 5 minutes. If desired, an individual can turn over so that the water droplets fall on their backs for another 2½ to 5 minute session.

In a further modification of the above embodiment, the aforementioned apparatus includes a mechanism for positioning the water distribution pipes about 2 to 3 feet above a support having room for an individual to lye thereon and for lowering the water distribution pipes to a distance above an individual's body by about 1 to about 2½ feet of the individual's horizontal body.

A second embodiment of the invention relates to a method for reducing the weight of a human individual. The method includes the step of providing a therapeutic shower including a water heater for supplying a mass of heated water at a temperature of about 25° C. to about 30° C. and a one-half horse power water pump. Ten generally horizontal sections of about one-half inch diameter pipe are connected together by nine generally vertical sections of pipe in a serpentine configuration 31 wherein the generally horizontal sections include a total of about 100 slightly upwardly directed apertures 33 each with an opening of about 0.12 inches for spraying heated water droplets on a majority of the human body. In the preferred form, the droplets are sprayed upwardly at an angle of about 30 degrees to about 45 degrees and up to about 60 degrees with the horizontal sections vertically separated from one another.

Spraying a majority of a the human body with heated water droplets for a period of about two and one-half minutes to five minutes three times a day is believed to be effective in reducing weight. In addition, heaters are provided for directing heated air onto the human body and drying the human body. Finally, a moisturizing lotion is applied to the human body after each treatment.

The invention will now be described in connection with the accompanying figures wherein like reference numerals are used to designate like parts.

DESCRIPTION OF THE PREFERRED
EMBODIMENTS OF THE INVENTION

Figure 1:
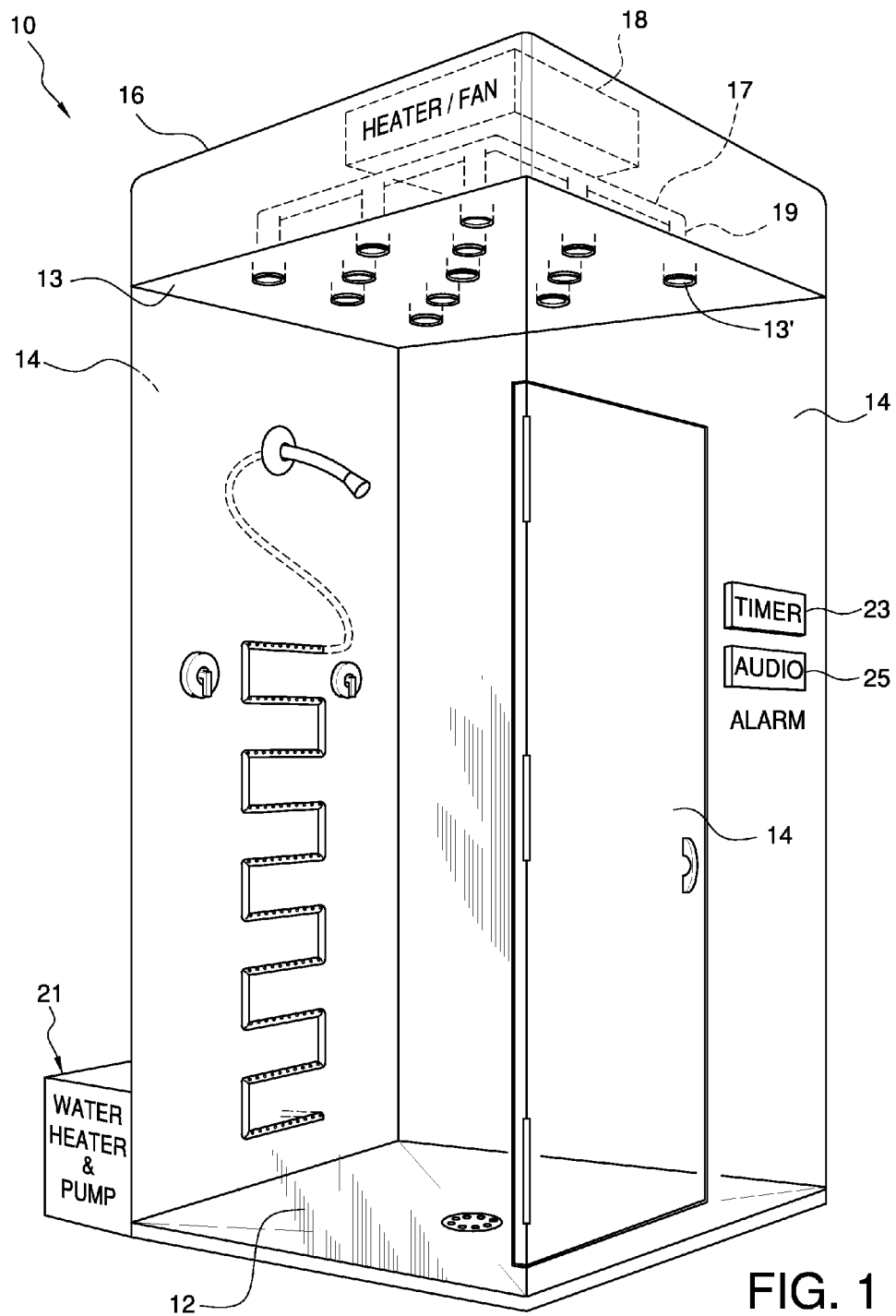
FIG. 1 is a perspective view of a shower enclosure in accordance with a first embodiment of the invention.
Figure 2:
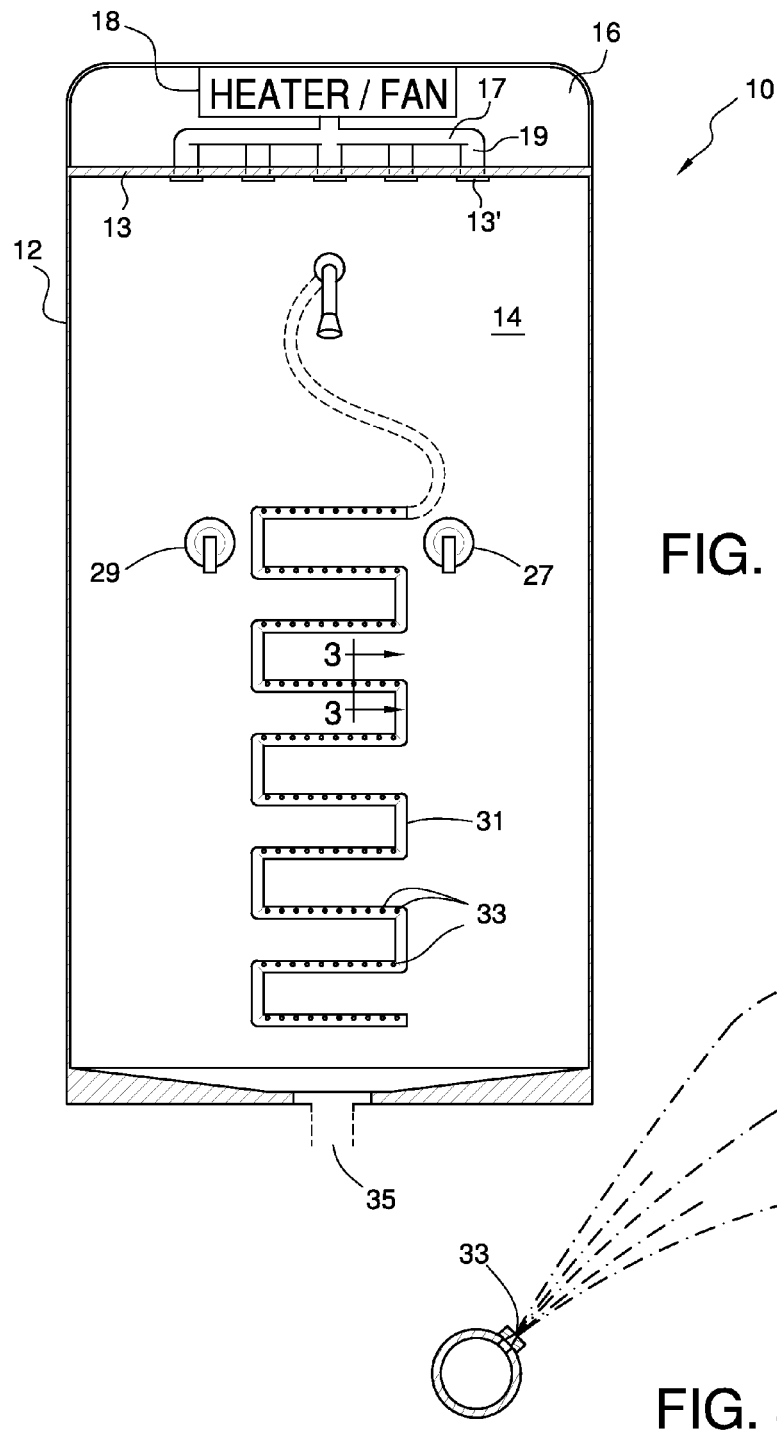
FIG. 2 is a schematic illustration of a serpentine water distributor in accordance with the second embodiment of the invention.
Figure 3:
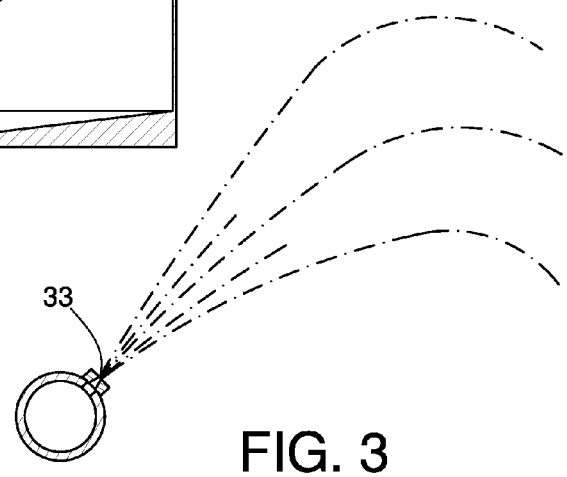
FIG. 3 is a schematic illustration showing the pathway of water droplets as distributed in a further embodiment of the invention.
Figure 4:
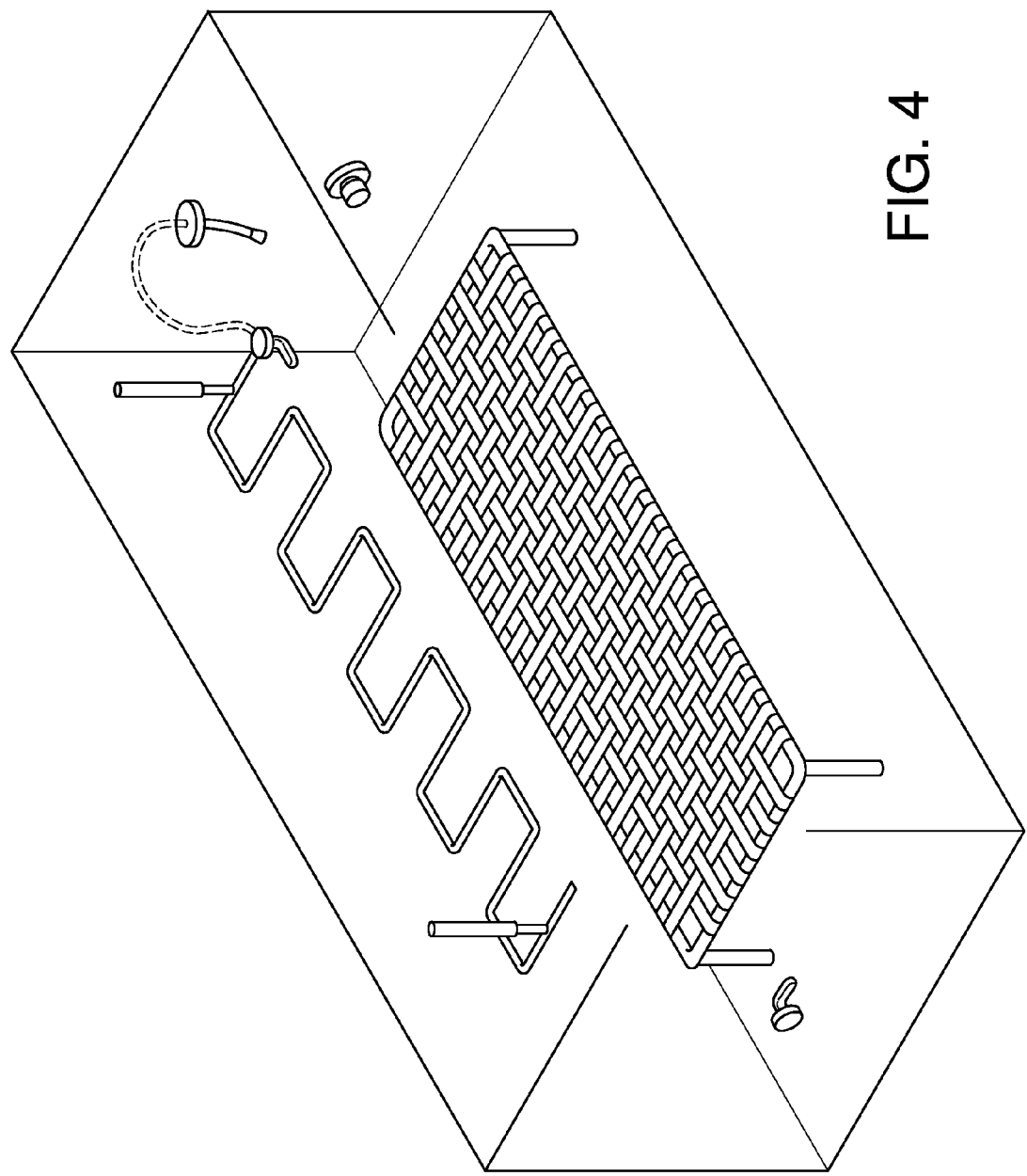
FIG. 4 is a schematic illustration showing a shower enclosure and assembly in accordance with the preferred embodiment of the invention; and, FIG. 5 is a flowchart illustrating a method for weight reduction in accordance with an additional embodiment of the invention.
Figure 5:
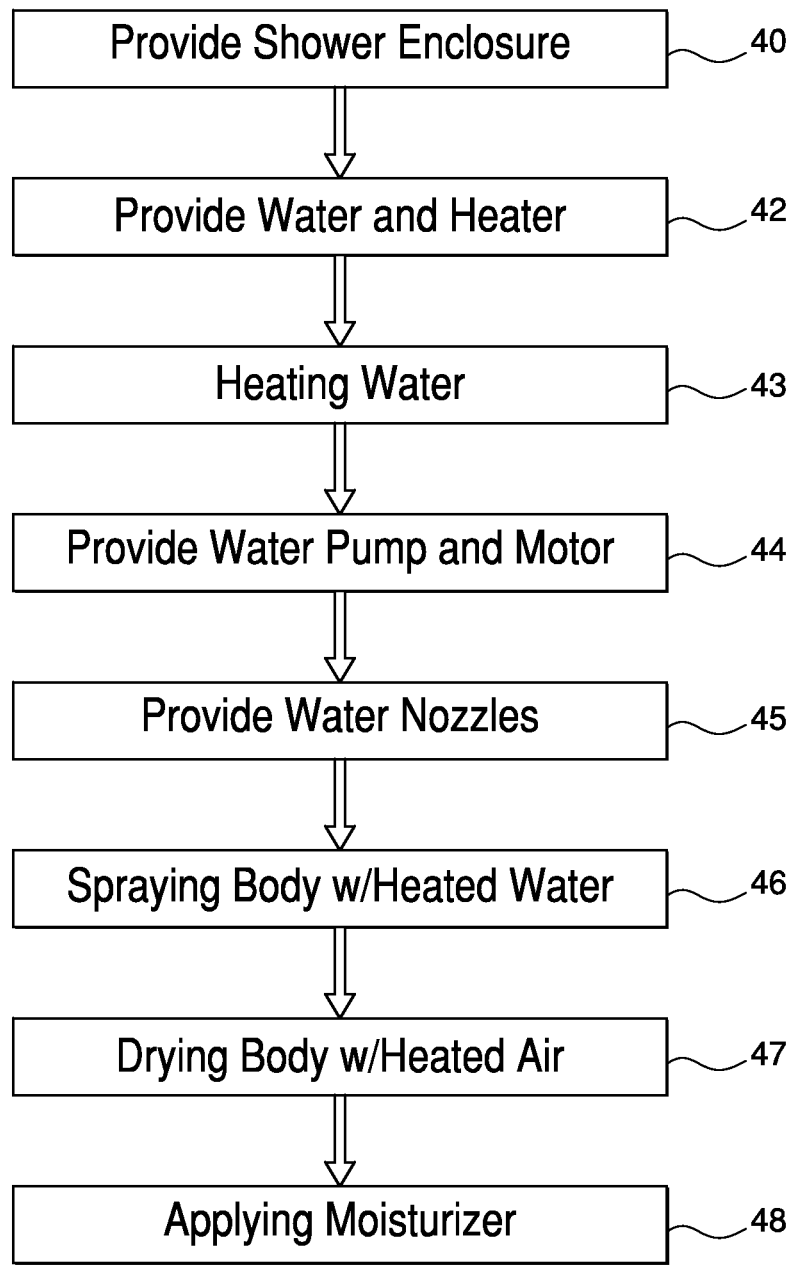

Referring now to the drawings and more specifically to FIG. 1, there is shown generally at 10 a therapeutic shower enclosure of the present invention. The enclosure comprises a bottom and a first wall 12, two sidewalls 14, a top 13, and a door 14 permitting access to by individual into the enclosure 10.

A molded shell 16 is secured over the top 13 of the enclosure and has molded therein distribution channels 17 which are connected to an air blower 18, and ducts 19 to provide an air stream that is convected downwardly in to the enclosure and in the direction of an individual. The hot air is then dispersed through vents 13' in the molded top. In this way, the user is subjected to a hot dry air stream to undergo therapeutic effects as will be described herein below.

It is also contemplated that in place of a hot dry air stream, infrared lights can be disposed in an upper portion of the enclosure 10 to dry the individual. In the preferred embodiment of the invention, the ideal zone for therapeutic heat treatment during the drying provides a temperature of between 31° C. and about 35° C. (88° F. to about 95° F.) at which temperature a human individual can accept the heat treatment for approximately 20 minutes. It is in this zone that we obtain some therapeutic effects and the physiological reaction to heat. For people who have exercised they will appreciate a range which is more elevated, for example, 35° C. to 40° C. Also after a person has acclimated to the therapeutic shower enclosure they can gradually increase the temperature range. It should be recognized that the temperature of air in the enclosure should be approximately 40° C. (104° F.) and the speed of the air on the user's body should not exceed about 0.2 m/s. It has been recognized that for temperatures of 38° C. at one hour of exposure, a person can develop a heat stroke. At 46° C. the temperature of the skin will be high enough to start exposing burn rashes. The more tolerant person can exceed 50 minutes at 52° C. In a sauna one can attain temperatures as high as 85° C. but a person should not be subjected to those for long periods of time and it is recommended that the period should be between 5 to 15 minutes maximum.

The enclosure in a preferred embodiment has a width of about 6 to 6½ feet (183 to 198 cms) and a depth from front to back of at least 30 to 36 inches (76 to 91 cms) so that an individual can lay down on a horizontal support. The support includes a series of openings of about 1 square inch to 2 square inches separated by solid portions between the openings so that water can pass through the support. The mechanism for spraying water onto an individual may also be used to raise and lower the water sprayers to allow an ingress and egress from the shower stall and to bring the sprayer within 18 to 36 inches (46 to 91 cms) from above an individual's body. Also, there is one or more valves 27, 29 so that a spray of water will not be directed onto an individual's head and face and also to stop the flow of water. Finally, the assembly includes a timer 23 and an audio alarm 25 to indicate that a 2½ to 5 minute treatment session is over.

The shower enclosure also includes a bottom or a base with a drain therein, two side walls, and a door forming a fourth wall and a molded top including a plurality of downwardly directed channels or passageways for directing a flow of heated air onto an individual. The air is heated to a temperature between 30° C. to 35° C. to dry an individual.

The invention also contemplates a method for weight reduction that comprises or consists of the following steps. A first step 40 provides a therapeutic shower enclosure having a first wall and a water outlet extending outwardly from an upper portion of a first wall. The step 43 is heating the water. The step 45 is to provide the water nozzles. The steps 47 is drying body with heater air.

A second step 42 provides a water supply and heater for heating a mass of water to a temperature of about 25° C. to 30° C., a one-half horsepower water pump and a serpentine array of nozzles arranged in ten rows of horizontally disposed upwardly directed openings that form an upwardly directed stream of water that are directed upwardly at an angle of about 30° to about 60° from horizontal. The horizontal disposed openings i.e. row are connected together by nine vertically disposed ½" tubular pipes or passages.

In a third step 44 a majority of an individual's body is subjected to a wall of hot water openings at relatively low pressure for a period of 2½ to 5 minutes. In step 46 the water treatment is followed by subjecting the individual to a flow of heated air at a temperature of about 35° C. to about 40° C. (104° F.) for a period of about 5 minutes.

When an individual's body is dry, a moisturizing lotion or cream is applied to the body in step 48 to avoid drying out the skin.

While the invention has been described in connection with its preferred embodiments it should be recognized that changes and modifications may be made therein without departing from the scope of the appended claims.

What is claimed is:

1. A therapeutic shower assembly for weight reduction, said assembly consisting of:
    a horizontal supporting including a plurality of openings to allow water to pass therethrough and for supporting an individual's body in a horizontal position, a shower enclosure with a width of at least 72 inches (183 cms), a depth of at least 30 inches (76 cms) for accommodating said support with an individual lying thereon;
    a water heater for heating a mass of pressurized water to a temperature of about 25° C. to 30° C., a source of water pressure and a horizontal serpentine pipe including a plurality of parallel portions and a plurality of upwardly directed small openings on each of said parallel portions for directing a stream of heated water upwardly at an angle of about 45° above horizontal and said serpentine pipe disposed over and across an individual's body;
    a first valve disposed in said serpentine pipe for stopping a flow of heated water to a portion of said pipe to thereby avoid directing water onto the head of an individual, a second valve disposed in said pipe for stopping the stream of heated water, a second heater for heating a mass of air to a temperature of about 30° C. to about 35° and a blower for directing the heated air onto and over the individual's body;
    a mechanism for raising said horizontal serpentine pipe to provide access to said support and for lowering said serpentine pipe to a distance of about 12 to 18 inches (30 cms to about 61 cms) above an individual's body; and
    a timer and an audio alarm to indicate that the time for a treatment has lapsed.

2. A therapeutic shower assembly according to claim 1, in which said second heater is an infra-red light bulb.

3. A therapeutic shower assembly according to claim 1, which includes a blower for directing a flow of heated air onto the body of an individual and in which said heated air is heated to a temperature of about 30° C. to about 35° C.

4. A therapeutic shower assembly according to claim 1, in which said upwardly directed small openings are directed upwardly at an angle of between 30° and 60° above horizontal and in which said water heats said water to a temperature of about 25° C. to 30° C.

5. A therapeutic shower assembly according to claim 4, in which said serpentine pipe includes a plurality of parallel portions that extend above and across an individual's body.

6. A therapeutic shower assembly according to claim 5, in which said shower enclosure has a width of at least about 72 inches (183 cms), a depth of at least 30 inches (76 cms) and in which said support includes a plurality of openings for allowing water to pass therethrough.

7. A therapeutic shower assembly according to claim 5, in which said serpentine pipe includes a second valve for cutting off a flow of heated water to a portion of said pipe that extends across the head of an individual.

8. A therapeutic shower assembly according to claim 7, in which said assembly includes a mechanism for raising said horizontal serpentine pipe to provide access and egress to said support and for lowering said serpentine pipe to a distance of about 12 inches (30 cms) to 24 inches (61 cms) above an individual's body.

9. A therapeutic shower assembly according to claim 8, which includes a timer and an audio warning to indicate when a 2½ to 5 minute treatment has lapsed.

10. A method for reduction of weight for a human individual consisting of the steps of:
    providing a therapeutic shower including a water heater for supplying a mass of heated water at a temperature of about 25° to about 30° C. and a one-half horsepower water pump, ten generally horizontal sections of about one-half inch diameter pipe connected together by nine generally perpendicular sections of pipe in a serpentine configuration and wherein said generally horizontal sections include a total of about 100 slightly upwardly directed apertures each with an opening of about 0.12 inches for spraying heated water droplets onto a majority of a human body;
    spraying the entire human body excluding their head with heated water droplets for a period of about 2½ minutes to 5 minutes three times a day;
    providing a heater for directing heated air at a temperature of about 35° C. to about 40° C. onto the human body for drying the human body; and
    applying a moisturizing lotion to the dry human body after each treatment.

* * * * *